United States Patent [19]
Nonomura et al.

[11] Patent Number: 6,083,916
[45] Date of Patent: *Jul. 4, 2000

[54] PHARMACEUTICAL PRODUCT FOR APPLICATION TO UTERUS MUCOSA

[75] Inventors: Muneo Nonomura, Toyonaka; Tomomichi Futo, Osaka; Hisayoshi Shimizu, Takatsuki, all of Japan

[73] Assignee: Takeda Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/050,085

[22] Filed: Mar. 30, 1998

[30] Foreign Application Priority Data

Apr. 4, 1997 [JP] Japan .................................. 9-086191

[51] Int. Cl.$^7$ ............................ A61K 38/08; A61K 38/09
[52] U.S. Cl. ........................... 514/15; 424/426; 424/430; 424/434; 128/113.1; 128/114.1; 128/115.1; 128/800; 128/834; 128/839; 530/828
[58] Field of Search ............................. 514/15; 424/426, 424/430, 434; 128/113.1, 114.1, 115.1, 800, 834, 839; 530/828

[56] References Cited

U.S. PATENT DOCUMENTS

| | | | |
|---|---|---|---|
| 3,880,991 | 4/1975 | Yolles . | |
| 3,993,057 | 11/1976 | Ramwell | 128/130 |
| 4,374,121 | 2/1983 | Cioca | 424/19 |
| 4,495,934 | 1/1985 | Shaw, Jr. | 128/130 |
| 4,585,651 | 4/1986 | Beck et al. | 424/88 |
| 5,224,493 | 7/1993 | Sawan et al. | 128/832 |
| 5,340,585 | 8/1994 | Pike et al. | 424/426 |
| 5,574,011 | 11/1996 | Tien | 514/14 |

FOREIGN PATENT DOCUMENTS

| | | |
|---|---|---|
| 5-24129 | 4/1993 | Japan . |
| 97/27840 | 8/1997 | WIPO . |

OTHER PUBLICATIONS

Physician's Desk Reference, 53$^{rd}$ ed., p. 2483, 1999.
Donna Van Wynsberghe et al. "Human Anatomy and Physiology" 3rd Ed., McGraw–Hill, Inc. NY., 1995.
Patent Abstracts of Japan, Vol. 018, No. 233, Apr. 28, 1994 & JP 06 022995 A, Feb. 1, 1994 *abstract*.
Masaharu Asano et al., "In Vivo Characteristics of Low Molecular Weight Copoly(L–Lactic Acid/Glycolic Acid) Formulations with Controlled Release of Luteinizing Hormone–Releasing Hormone Agonist", Journal of Controlled Release, Vol. 9, No. 2, Jul. 1989, pp. 111–122.
Masaharu Asano et al., "Biodegradability of hot–pressed poly(lactic acid) formulation with controlled release of LH–RH agonist and its pharmacological influence on rat prostate", Makromol. Chem. Rapid Commun. Vol. 6, No. 7, 1985, pp. 509–513.

*Primary Examiner*—F. T. Moezie
*Attorney, Agent, or Firm*—Wenderoth, Lind & Ponack, LLP.

[57] ABSTRACT

A drug comprising either a peptide having the LH-RH action or an LH-RH antagonist is carried on an intrauterine contraceptive device (IUD) so as to be able to provide controlled release. Once the IUD is put in the uterus, the carried drug is gradually released over such a prolonged period of treatment time as, for example, several months to be continuously absorbed through the uterus mucosa or the vagina mucosa. This construction makes it possible to reduce the patient's pain and such a troublesomeness as frequent drug administration and continuously administer a necessary drug over a prolonged period of time while taking a contraceptive measures.

2 Claims, 2 Drawing Sheets

PHARMACEUTICAL PRODUCT FOR APPLICATION TO UTERUS MUCOSA

BACKGROUND OF THE INVENTION

1. Field of the Invention

The present invention relates to a pharmaceutical product for application to the uterus mucosa, which carries a drug comprising a peptide having the luteinizing hormone releasing hormone (hereafter referred to only as 'LH-RH') action, an LH-RH antagonist or the like on an intrauterine contraceptive device (hereafter referred to as 'IUD') and is adjusted to be able to administer the drug over a prolonged period of time while taking a contraceptive measures by being fitted in the uterus or the like.

2. Description of the Prior Art

In order to treat breast cancer, uterus cancer, endometriosis or central precocious puberty, an LH-RH agonist, i.e. a peptide having the LH-RH action, and an LH-RH antagonist or the like are administered. However, these drugs can be hardly absorbed through the alimentary canal, so that there exist as conventional drugs for administration an injection drug to be administered by injection and a vaginally administered drug to be absorbed through the vagina mucosa rapidly, for example, as disclosed in Japanese Patent Publication No. Hei 5-24129.

3. Problems Presented by the Prior Art

The injection drug causes pain to a patient when administered and besides has to be administered for a long time so as to cure the above-mentioned diseases. Therefore, either of the above drugs required so frequent administration that it was troublesome.

In order to solve this problem, a drug having the property of providing controlled release is prepared as an injection drug by forming it into microcapsules and the like so as to lengthen its administration interval to, for example, four weeks or the like. However, this way entails a problem that the patient cannot be relieved from the pain the patient experiences when the drug is administered and besides the drug cannot be interrupted nor changed once it is administered.

Additionally, the patient should not become pregnant because the therapy for the above-mentioned diseases is likely to exert a bad influence on an embryo. Consequently, there was caused a problem that the patient must undergo a non-hormone contraceptive treatment such as fitting an IUD separately from the administration of the above drug.

SUMMARY OF THE INVENTION

The present invention has an object to solve the foregoing problems and provide a pharmaceutical product for application to the uterus mucosa, capable of softening the patient's pain as well as reducing the number of administration so as to decrease such a troublesomeness as frequent administration and continuously administering a necessary drug over a prolonged period of time while taking a contraceptive measures.

In order to accomplish the object, the present invention has constructed a pharmaceutical product for application to the uterus mucosa as follows.

A first invention is characterized in that a drug comprising either a peptide having the LH-RH action or an LH-RH antagonist is carried on an intrauterine contraceptive device so as to be able to provide controlled release.

Here the construction of carrying so as to be able to provide controlled release means a construction able to gradually release a carried drug. Concrete examples of such construction can be listed as follows:

A capsule type means for controlled release which comprises covering pharmaceutical particles with a high polymer film and diffusing the pharmaceutical particles gradually through the high polymer film;

A matrix type means for controlled release which comprises dispersing pharmaceutical particles in a high polymer material of a spherical shape or the like and gradually diffusing them from a surface of the high polymer material;

A means for controlled release with the use of an osmotic pressure pump, which comprises a container formed from a semi-permeable membrane and provided with a delivering outlet at one portion thereof and delivers through the outlet a drug accommodated in the container by an osmotic pressure of the moisture invading from around the container;

A means for controlled release which employs a container provided with pores in its peripheral wall instead of the foregoing semi-permeable membrane;

A closure-type means for controlled release which comprises a container accommodating a drug and covered with a closure formed from a biodegradable or soluble high polymer; and A pulse-type means for controlled release which comprises a plurality of small chambers arranged in series and accommodating a drug, a partition wall of each chamber being made of a biodegradable or soluble high polymer.

However, the construction of carrying so as to be able to provide controlled release according to the present invention is not limited to those means.

When carrying the above drug on the intrauterine contraceptive device (IUD), an excipient or the like additives are mixed if needed. Examples of them are listed below:

Water and polyatomic alcohols as a solvent for dissolving the drug;

Sugar-alcohols, sugars, polysaccharides, gelatinizer and grease as an excipient for dispersing the drug and keeping it dispersed;

Sorbitan fatty acid esters and polyoxyethylene sorbitan fatty acid esters as a surfactant; and Inorganic salts, organic acid salts, inorganic bases and inorganic acids as a pH regulator or an osmotic pressure regulator.

The above-mentioned IUD may take such a shape as having been widely used up to now. Further, it may be opened instead of being closed in the shape of a ring. Generally, it means an IUD to be fitted in the uterus but may be fitted in the vagina.

A second invention is characterized in that an intrauterine contraceptive device is formed from a biodegradable high polymer and carries a drug so as to be able to provide controlled release of the drug.

Here the biodegradable high polymer means a high polymer material gradually decomposing in vivo. Copolymers of lactic and glycolic acids (PLGA), polymers of lactic acid (PLA), copolymers of butyric and glycolic acids (PBGA), esters of these polymers, a complex consisting of at least two of these polymers or esters and collagen can be listed as its examples but it is not limited to these ones.

Further, besides leuprorelin acetate, an LH-RH agonist and the LH-RH antagonist, for example, the following ones can be used as the above drug:

Follicle Estrogen or Progestogen;
   allylestrenol, estradiol benzoate, estriol benzoate, estradiol, estriol, ethinylestradiol, gestnorone caproate, hydroxyprogesterone caproate, estradiol valerate, estrogens conjugated, chlormadinone acetate, medroxyprogesterone acetate, dydrogesterone, estradiol dipropionate, estriol tripropionate, norethisterone, pregnanediol, progesterone, fosfestrol, and mestranol.

Antipyretic, analgestic and anti-inflammatory agents;
   actarit, aspirin, aspirin·ascorbic acid, aspirin·dialuminate, acetaminophen, acemetacin, alclofenac, alminoprofen, ampiroxicam, amfenac sodium, isopropylantipyrine, ibuprofen, indometacin, indometacin farnesil, ethenzamide, etodolac, epirizole, emorfazone, tiaramide hydrochloride, tinoridine hydrochloride, tramadol hydrochloride, buprenorphine hydrochloride, oxaprozin, obelon, camphor·sodium salicylate, cleamine A, cleamine S, ketophenylbutazone, ketoprofen, chondroitin sulfate sodium-sodium salicylate, sasapyrine, salicylamide, sodium salicylate, saridon, salsocain, zaltoprofen, simetride·anhydrous caffeine, eptazocinehydrobromide, ergotamine tartrate·anhydrous caffeine, butorphanol tartrate, diclofenac sodium, diflunisal, sulindac, sulpyrine, tiaprofenic acid, tenoxicam, tolfenamic acid, tolmetin sodium, nabumetone, naproxen, neo vitacain, piroxicam, phenacetin, fenoprofen calcium, fenbufen, flufenamic acid, flufenamic acid aluminium, flurbiprofen, flurbiprofen axetil, floctafenine, bucolome, pranoprofen, pentazocine, proglumetacin maleate, migrenin, dimetotiazine mesilate, metiazinic acid, mefenamic acid, mofezolac, loxoprofen sodium, lobenzarit disodium, and an extract from inflammatory rabbit skin inoculated by vaccinia virus.

Metabolic inhibitors;
   6-mercaptopurine riboside, enocitabine, carmofur, cytarabine, cytarabine ocphosfate, tegafur, tegafur·uracil, doxifluridine, hydroxycarbamide, fluorouracil, methotrexate, and mercaptopurine.

Alkylating agents;
   ifogfamide, nitrogen mustard-N-oxide hydrochloride, nimustine hydrochloride, carboquone, cyclophosphamide, dacarbazine, thiotepa, improsulfan tosilate, busulfan, mitobronitol, melphalan, ranimustine, and estramustine phosphate sodium.

Anti-tumor and antibiotic agents;
   actinomycin D, aclarubicin hydrochloride, idarubicin hydrochloride, epirubicin hydrochloride, daunorubicin hydrochloride, doxorubicin hydrochloride, pirarubicin hydrochloride, bleomycin hydrochloride, zinostatin stimalamer, neocarzinostatin, mitomycin C, bleomycin sulfate and peplomycin sulfate.

Anti-tumor plant agents;
   etoposide, irinotecan hydrochloride, vincristine sulfate, vindesine sulfate, and vinblastine sulfate.

Other anti-tumor agents;
   aceglatone, ubenimex, L-asparaginase, fadrozole hydrochloride hydrate, procarbazine hydrochloride, mitoxantrone hydrochloride, carboplatin, tamoxifen citrate, toremifene citrate, krestin, medroxyprogesterone acetate, cisplatin, schizophyllan, sobuzoxane, tretinoin, nedaplatin, picibanil, flutamide, pentostatin, porfimer sodium, and lentinan.

Anti-endometriosis agents or anti-uterine fibroids agents;
   nafarelin acetate, buserelin acetate, dydrogesterone, danazol and ethinylestradiol·norgestrel.

However, the above drug is not limited to these ones but at least two of them may be compounded when needed.

A third invention comprises defining the drug set forth in the second invention to either a peptide having the LH-RH action or an LH-RH antagonist.

A drug carried on an IUD is gradually released to be continuously absorbed through the uterus mucosa or the vagina mucosa for such a long period of treatment time as, for example, several months once the IUD is put in the uterus. Besides, during this treatment term, the fitted IUD prevents pregnancy.

If the IUD is formed from a biodegradable high polymer, it gradually decomposes by itself while providing controlled release of the drug and will completely decompose after the elapse of an administration term. Therefore, it need not be removed from the living body.

The present 1st to 3rd invention produces the following advantages because it is constructed and functions as mentioned above.

(1) The present invention can administer a necessary drug without giving such a pain as caused by injection and besides can do it continuously over such a prolonged period of time as at least several months if only once fitted. Additionally, since the fitting itself is a contraceptive measures, no other contraceptive measures is needed to result in the possibility of reducing the patient's pain and the troublesomeness such as frequent administration.

(2) The drug administration can be interrupted or changed at an optional time by removing the fitted IUD. Therefore, it is possible to make a proper drug administration depending on the condition of the patient, differently from the conventional technique which employs an injection drug having the property of providing controlled release.

Moreover, the pharmaceutical product for application to the uterus mucosa according to the second or the third invention has the following characteristic:

(3) An IUD being made of a biodegradable high polymer, it is not necessary to remove the IUD from the living body because it is completely decomposed after the elapse of an administration term. Only the fitting of this IUD is sufficient when administering the drug. This can further lessen the troublesomeness experienced when administering the drug.

DETAILED DESCRIPTION OF PREFERRED EMBODIMENT

First Embodiment

Figure 1:
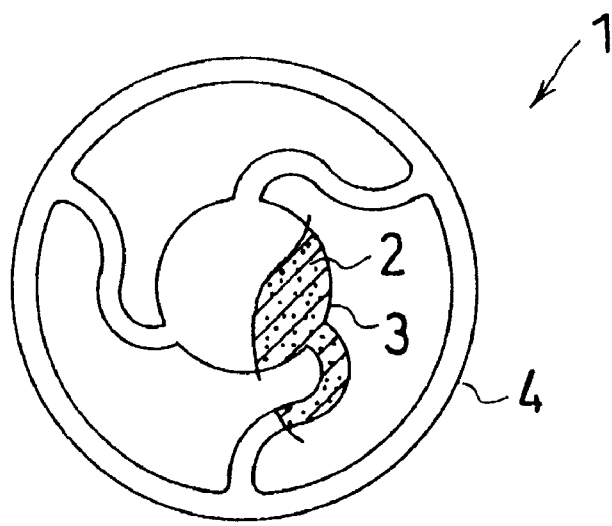
FIG. 1 is a sectional view of a pharmaceutical product for application to the uterus mucosa, showing a first embodiment.

A pharmaceutical product 1 for application to the uterus mucosa according to a first embodiment of the present invention as shown in FIG. 1 was formed by dispersing a drug 2 such as a peptide having the LH-RH action in a biodegradable high polymer 3 and molding it to a predetermined shape of IUD 4 by a casting mold.

When such IUD 4 is fitted in the uterus, the biodegradable high polymer 3 gradually decomposes and at the same time the drug 2 provides controlled release to be efficiently absorbed through the uterus mucosa over a prolonged period of time.

And after the elapse of a predetermined period of time, for example, three months, while the drug 2 carried on the IUD 4 is completely released, the IUD 4 itself disappears from the uterus with the whole biodegradable high polymer 3 decomposed.

Then another new IUD 4 carrying the drug 2 is fitted in the uterus to continue the treatment.

Notably, it is possible to interrupt the treatment at an optional time by taking the IUD 4 away from the uterus. When changing the amount and term for controlled release as well as the kind of the drug, a new IUD 4 carrying a desired drug so as to be able to provide controlled release of the drug for a desired period of time is fitted in the uterus after the old IUD 4 has been removed from the uterus.

EXAMPLE 1

596 mg of leuprorelin acetate, an LH-RH agonist and 94 mg of gelatine were dissolved in 0.5 g of water to prepare an aqueous solution. Meanwhile, 4.78 g of 75/25 (w/w) copolymer of lactic and glycolic acids having a molecular weight of about 14,000 (PLGA) was dissolved in 8.0 g of dichloromethane. Then this solution was added to the above aqueous solution to prepare a W/O emulsion and cool it to 19° C.

Next, this emulsion was dispersed into 1 liter of 0.1% PVA solution preliminarily cooled to 19° C. to thereby make a (W/O)/W emulsion. This (W/O)/W emulsion was dried in water for three hours to volatilize the dichloromethane. Thereafter, the resulting microcapsules were scavenged through centrifugation and freeze dried.

Thus dried microcapsules were heat molded by a casting mold to obtain a pharmaceutical product for application to the uterus mucosa in a desired shape of IUD.

This pharmaceutical product continued to release leuprorelin acetate in the uterus over a period of at least one month.

EXAMPLE 2

433 mg of leuprorelin acetate was dissolved in 0.5 g of water to prepare an aqueous solution. Meanwhile, 3.83 g of poly-lactic acid (PLA) having a molecular weight of 17,000 was dissolved in 6.4 g of dichloromethane. This solution was added to the above aqueous solution to prepare a W/O emulsion and cool it to 15° C.

Next, this emulsion was dispersed into 1 liter of 0.1% PVA solution preliminarily cooled to 15° C. to make a (W/O)/W emulsion. Then this (W/O)/W emulsion was dried in water for three hours. The resulting microcapsules were scavenged through centrifugation and freeze dried. Thereafter, they were compression molded to a desired shape of IUD by a casting mold.

The obtained pharmaceutical product for application to the uterus mucosa continued to release leuprorelin acetate in the uterus over a period of at least three months.

EXAMPLE 3

500 mg of leuprorelin acetate was dissolved in 50 g of water to prepare an aqueous solutiqn. Meanwhile, 4.5 g of copolymer of butyric and glycolic acids having a molecular weight of about 18,500 (PBGA) was dissolved in 10 g of dichloromethane. This solution was added to the above aqueous solution to prepare a W/O emulsion.

Next, this emulsion was vacuum dried in a casting mold and compression molded to a desired shape of IUD. The obtained pharmaceutical product for application to the uterus mucosa continued to release leuprorelin acetate in the uterus over a period of at least one month.

EXAMPLE 4

5 g of leuprorelin acetate was dissolved in 50 g of water to prepare an aqueous solution. Meanwhile, 45 g of PLGA having the same grade as that used in Example 1 was dissolved in 100 g of dichloromethane. This solution was added to the above aqueous solution to prepare a W/O emulsion.

Next, this emulsion was dried at a temperature of 40° C. under a condition of 100 to 300 Torr by a vacuum drier. The resulting dried product was ground by a turbo-counter jet mill. The thus ground substance was accommodated in a casting mold and heat molded to obtain a pharmaceutical product for application to the uterus mucosa in a desired shape of IUD.

The obtained product continued to release leuprorelin acetate in the uterus over a period of at least one month.

EXAMPLE 5

4.5 g of 55/45 (w/w) copolymer of lactic and glycolic acids, PLGA having a molecular weight of about 20,000 was dissolved in 10 g of dichloromethane. 6.5 g of cisplatin, an antineoplastic (anticancer) agent was added to this solution so as to suspend it therein homogeneously with ultrasonic.

This suspension was accommodated in a casting mold and vacuum dried at room temperature to obtain a pharmaceutical product for application to the uterus mucosa in a desired shape of IUD.

The obtained pharmaceutical product continued to release cisplatin in the uterus over a period of at least one month.

Second Embodiment

Figure 2:
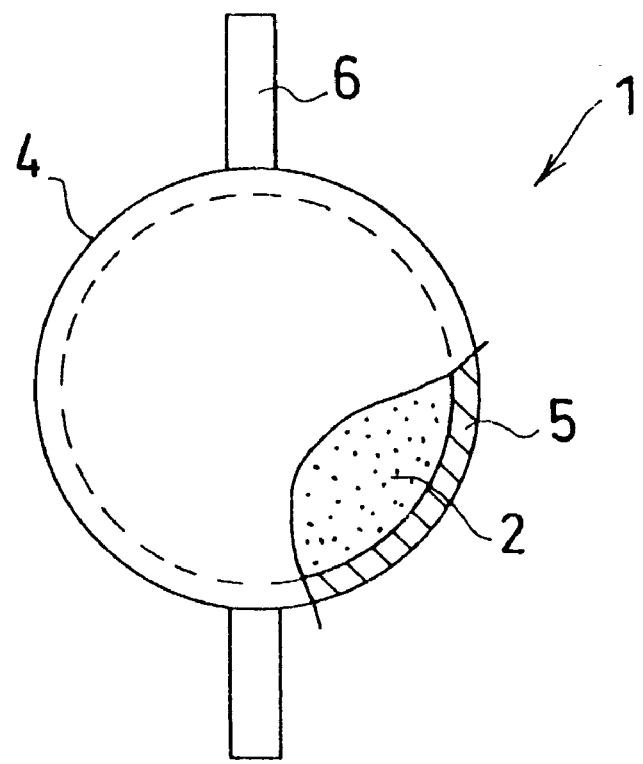
FIG. 2 is a view corresponding to FIG. 1 and showing a second embodiment.

A pharmaceutical product 1 for application to the uterus mucosa according to a second embodiment of the present invention as shown in FIG. 2 comprises a drug 2 enclosed in a diffusion controlled film 5 made of a high polymer material such as, for example, a copolymer of ethylene and vinyl acetate and then supported by silicon elastomer 6 or the like to be formed into an IUD 4.

The drug 2 carried on the IUD 4 gradually passes through the diffusion controlled film 5 and diffuses to be absorbed through the uterus mucosa. Since the transmission and diffusion of the drug decrease after a predetermined period of time has elapsed, this IUD 4 is removed from the uterus and a new IUD 4 is fitted if the administration is continued.

EXAMPLE 6

500 mg of leuprorelin acetate and 4.5 g of PLA having a molecular weight of about 25,000 were dissolved in 10 g of dichloromethane. This solution was dispersed into 1 liter of 0.1% PVA solution to prepare an O/W emulsion.

This O/W emulsion was dried in water for three hours. The resulting microcapsules were scavenged through centrifugation and freeze dried. The dried substance was suspended in silicon oil. This suspension was enclosed in a film made of a copolymer of ethylene and vinyl acetate and supported by silicon elastomer to obtain a pharmaceutical product for application to the uterus mucosa formed in a desired shape of IUD.

This pharmaceutical product continued to release leuprorelin acetate in the uterus over a period of at least three months.

Figure 3:
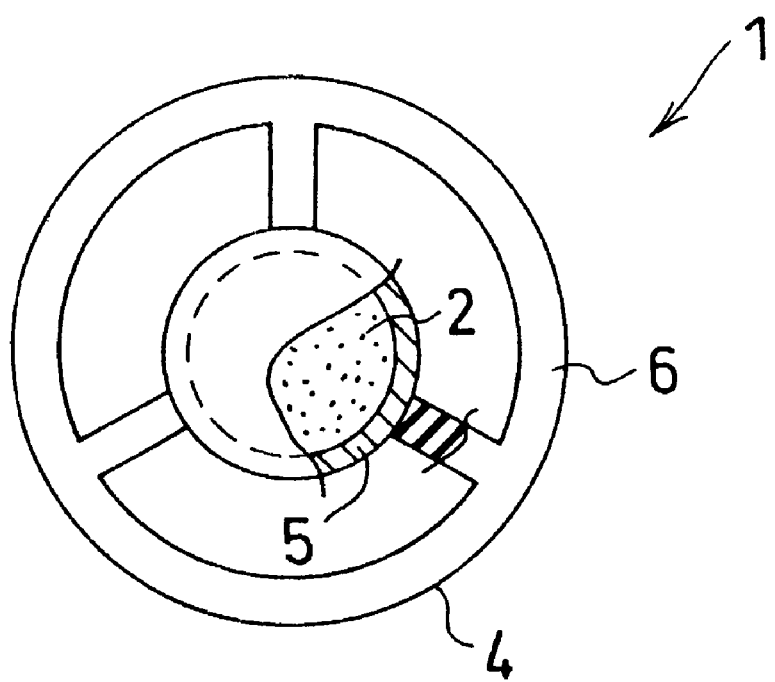
FIG. 3 is a view corresponding to FIG. 1 and showing a modification of the second embodiment.

The IUD 4 may take the shape of the modification shown in, for example, FIG. 3 or other shapes as far as they don't cause any abnormality to the living body when fitted.

Needless to say, the drug to be used is not limited to those shown in Examples 1 to 6. The term within which the drug can be administered for controlled release in the uterus can be suitably fixed to, for example, at least six months by controlling the amount and delivery speed of the drug to be carried as far as it does not cause any abnormality to the living body.

What is claimed is:

1. An intrauterine contraceptive device which is made from a biodegradable copolymer of lactic acid and glycolic acid and/or a biodegradable polymer of lactic acid, wherein leuprorelin acetate is comprised in the device, said device is applied to a patient for treatment of breast cancer, uterus cancer, endometriosis or central precocious puberty, and the release of the leuprorelin acetate from the device is prolonged.

2. A method for treating breast cancer, uterus cancer, endometriosis or central precocious puberty comprising administering to a patient in need of the treatment an intrauterine contraceptive device which is prepared from a biodegradable copolymer of lactic acid and glycolic acid and/or a biodegradable polymer of lactic acid, wherein leuprorelin acetate is comprised in the device and the release of leuprorelin acetate from the device is prolonged.

* * * * *